United States Patent
Pardhasaradhi et al.

(10) Patent No.: US 6,608,200 B1
(45) Date of Patent: Aug. 19, 2003

(54) PROCESS FOR THE PREPARATION OF N-(2,3-DIHYDROBENZO[1,4]DIOXIN-2-CARBONYL)PIPERAZINE

(75) Inventors: Malladi Pardhasaradhi, Secunderabad (IN); Gullapalli Kumaraswamy, Nacharam (IN); Arun Kanti Das, Hyderabad (IN); Nivedita Jena, Hyderabad (IN); Chembumkulam Kamalakshyamma Snehalatha Nair, Secunderabad (IN); Mudiganti Naga Venkata Sastry, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/266,991

(22) Filed: Oct. 7, 2002

(51) Int. Cl.[7] ............................................. C07D 405/06
(52) U.S. Cl. ....................... 544/377; 544/291
(58) Field of Search ......................... 544/377

(56) References Cited

U.S. PATENT DOCUMENTS 4,188,390 A * 2/1980 Campbell
4,287,341 A * 9/1981 Hess et al.
5,919,931 A * 7/1999 Murthy et al.
6,313,293 B1 * 11/2001 Chou et al.
6,313,294 B1 * 11/2001 Chou et al.

FOREIGN PATENT DOCUMENTS

GB 2171997 A * 9/1986

OTHER PUBLICATIONS

Luo et al Chemical Abstracts, vol. 135, No. 272988 (2001) Abstract for CN 1285353 (Feb. 28, 2001).*
Chou et al. J.Org. Chem. vol. 63, p. 10015–10017 (1998).*
Campbell et al. J.Med. Chem. vol. 30, p. 49–57 (1987).*

* cited by examiner

Primary Examiner—Emily Bernhardt
(74) Attorney, Agent, or Firm—Meyertons, Hood, Kivlin, Kowert & Goetzel P.C.; Eric B. Meyertons

(57) ABSTRACT

Described herein is an improved process for the preparation of N-(2,3-Dihydrobenzo[1,4]dioxin-2-carbonyl)piperazine which includes heating a reaction mixture ethyl of 2,3-dihydrobenzo[1,4]dioxin-2-carboxylate and piperazine. The reaction mixture is then subjected to series of washes and extraction to yield N-(2,3-Dihydrobenzo[1,4]dioxin-2-carbonyl)piperazine having a purity of greater than 99.9%.

4 Claims, No Drawings

PROCESS FOR THE PREPARATION OF N-(2, 3-DIHYDROBENZO[1,4]DIOXIN-2-CARBONYL)PIPERAZINE

FIELD OF THE INVENTION

The present invention relates to a process for the preparation of N-(2,3Dihydrobenzo[1,4]dioxin-2-carbonyl) piperazine.

BACKGROUND OF THE INVENTION

N-(2,3-Dihydrobenzo[1,4]dioxin-2-carbonyl) piperazine is an important intermediate for the preparation of an anti-hypertensive drug viz., doxazocin. Doxazocin is prepared by reaction of N-(2,3-Dihydrobenzo[1,4]dioxin-2-carbonyl)piperazine with 4-amino-2-chloro-6,7-dimethoxy quinazoline [J. Med. Chem., 1987, 30(1), 49]. However, it was observed that the product obtained by this condensation contained bis-amide as impurity. It makes the product unsuitable for pharmaceutical use as doxazocin base prepared by basification, on analysis showed purity of 91–94% only. Further purification of the base was very difficult due to its polymorphic nature. Large number of references are available mostly of patents (U.S. Pat. Nos. 6,140,334; 6,133, 269; 6,130,218) in which doxazocin base has been subjected to tedious purification procedures consisting of four to five steps in order to obtain pure doxazocin of pharmaceutical grade.

Pharmaceutical industry requires pure doxazocin (99.99%) for processing into solid dosage form. In our attempts to prepare pure doxazocin, we found that the purity and crystalline nature of doxazocin were dependent on the purity of N-(2,3-Dihydrobenzo[1,4]dioxin-2-carbonyl) piperazine that was used for the condensation. While it was easy to prepare 4-amino-2-chloro-6,7-dimethoxy quinazoline in high yield and purity, the preparation of N-(2,3-Dihydrobenzo[1,4]dioxin-2-carbonyl)piperazine posed several problems due to its contamination with the bis-amide impurity. It is glassy and difficult to work with. It is essential to evolve a method for the preparation of pure amide not contaminated with bis-amide, N-(2,3-Dihydrobenzo[1,4]dioxin-2-carbonyl)piperazine is a condensation product of ethyl 2,3-Dihydrobenzo[1,4] dioxin-2-carboxylate and piperazine [Equation 1].

Equation-1

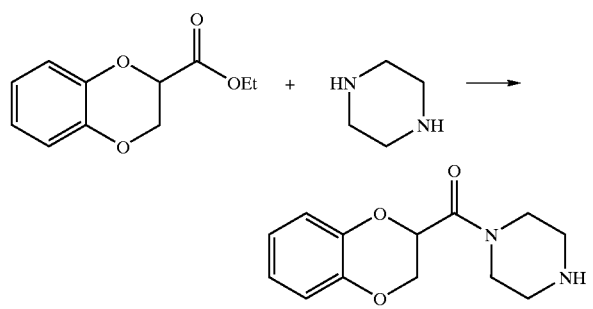

N-Acyl alkylenediamines were earlier prepared by the monoamidation of alkylenediamines with acid chlorides. The reaction requires the masking of diamines as monoacetates or hydrogen halides [J. Med. Chem.,1997, 20, 146]. The procedure is tedious and requires i) saponification of ester ii) treatment of the resulting acid with thionyl chloride to give the acid chloride and iii) amidation with piperazine hydrobromide in methanol. There is also one report of the synthesis of N-Acyl alkylenediamnines (94% yield) by direct monoamidation of esters [J. Org. Chem., 1998, 63, 10015]. In this procedure, ethyl 2,3-dihydrobenzo[1,4] dioxin-2-carboxylate and piperazine were heated under reflux for 3 h. The reaction mixture was partitioned between $CHCl_3$ and saturated aq. $NaHCO_3$. The organic layer was washed, dried and concentrated. However, N-(2,3-Dihydrobenzo[1,4]dioxin-2-carbonyl)piperazine prepared by the above method when coupled with 4-amino-2-chloro-6,7-dimethoxy quinazoline gave a product, which on subsequent basification, gave doxazocin base with 92–95% purity. In view of the above, it is necessary to develop an improved process for the preparation of high purity N(2,3-Dihydrobenzo[1,4]dioxin-2-carbonyl)piperazine without contamination with bis-amide.

OBJECTS OF THE INVENTION

The main objective of the present invention is to provide a process for the preparation of high purity N-(2,3-Dihydrobenzo[1,4]dioxin-2-carbonyl)piperazine of Formula 1.

Another object of the present invention is to provide N-(2,3-Dihydrobenzo[1,4]dioxin-2-carbonyl)piperazine free from bis-amide and other impurities by simple acid base work-up procedure.

Formula-1

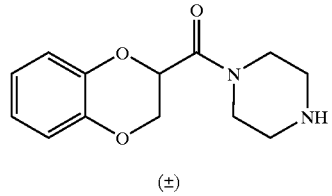

(±)

SUMMARY OF THE INVENTION

Accordingly, the present invention provides an improved process for the preparation of N-(2,3-Dihydrobenzo[1,4] dioxin-2-carbonyl)piperazine which comprises heating a reaction mixture ethyl of 2,3-dihydrobenzo[1,4]dioxin-2-carboxylate and piperazine with a molar ratio of carboxylate to piperazine in the range of 1:2 to 2:1, under nitrogen atmosphere, at a temperature in the range of 70–90° C. for a period of 3–15 hrs, cooling the above said reaction mixture to a temperature of 25–30° C. and dissolving it in chloroform followed by washing with saturated sodium bi-carbonate solution and water respectively, acidifying the organic layer by about 10% HCl to a pH ranging between 1 to 4, separating the organic layer and washing the aqueous layer with chloroform, basifying the aqueous layer with sodium bicarbonate to a pH ranging between 7 to 9 followed by extracting with chloroform and evaporating the chloroform to obtain the final desired product in amorphous solid form.

In an embodiment of the present invention the reaction mixture is heated for a period preferably in the range of 5–12 hrs.

In yet another embodiment the temperature used in heating reaction mixture is preferably in the range of 75–80° C.

In still another embodiment the purity of the compound N-(2,3-Dihydrobenzo[1,4]dioxin-2-carbonyl)piperazine obtained is in the range of 99.3–99.9%.

DETAIL DESCRIPTION OF THE INVENTION

In the improved process for the preparation of N-(2,3-Dihydrobenzo[1,4]dioxin-2-carbonyl)piperazine, ethyl 2,3-dihydrobenzo[1,4]dioxin-2-carboxylate and piperazine were reacted under a blanket of nitrogen at a temperature preferably in the range of 70–90° C. for a period preferably in the range of 5–12 h. The reaction mixture on cooling was taken into chloroform. The chloroform layer is acidified to a pH preferably in the range of 4–2. The aqueous layer was basified using solid NaHCO$_3$ to a pH preferably in the range of 7–8. It is again extracted into chloroform, dried and evaporated to give pure N-(2,3-Dihydrobenzo[1,4]dioxin-2-carbonyl) piperazine as a white solid without any contamination. Pharmaceutical grade doxazocin is prepared with this amide in a further process.

The following examples are given by way of illustration of the present invention and therefore should not be construed to limit the scope of the present invention.

EXAMPLE 1

Piperazine (101.3 g, 1.175 moles) and ethyl 1,3-Dihydrobenzol [1,4]dioxin-2-carbonyl(200 g, 0.96 moles) were taken into a round bottom flask provided with a stirrer, thermowell, and distillation setup. The reaction mixture was heated for 4 h to reach an internal temperature of about 75° C. while stirring. It was cooled to room temperature, dissolved in chloroform (200 ml) and washed with saturated sodium bicarbonate solution (1×150 ml) followed by water wash (3×150 ml). The organic layer was acidified to pH 2 with 10% HCl (600 ml). The organic layer was separated and aqueous layer washed with chloroform (3×100 ml). The aqueous portion was basifed with solid sodium bicarbonate to pH 8 and was extracted with chloroform (5×150 ml). The chloroform layer was evaporated to yield an amorphous solid powder (145 g, 61% yield), purity 99.9%.

EXAMPLE 2

Piperazine (10.13 g, 0.1175 moles) and ethy 2,3-dihydrobenzo[1,4]dioxin-2-carboxylate (20 g, 0.096 moles) were taken into a round bottom flask provided with a stirrer, thermowell and distillation setup. The reaction mixture was heated for 10 h to reach an internal temperature of about 75° C. while stirring. It was cooled to room temperature, dissolved in chloroform and washed with saturated sodium bicarbonate solution followed by water. The organic layer was acidified to pH 2 with 10% HCl. The organic layer was separated and aqueous layer washed with chloroform. This aqueous portion was basified with solid sodium bicarbonate to pH 8 and was extracted with chloroform. The chloroform layer was evaporated to yield an amorphous solid powder (21.67 g, 89.5% yield) purity 99.9%.

EXAMPLE 3

Piperazine (8.2 g, 0.096 moles) and ethyl 2,3-dihydrobenzo [1,4]dioxin-2-carboxylate (20 g, 0.096 moles) were taken into a round bottom flask provided with a stirrer, thermowell and distillation setup. The reaction mixture was heated for 10 h to reach an internal temperature of about 75° C. while stirring. It was cooled to room temperature, dissolved in chloroform and washed with saturated sodium bicarbonate solution followed by water. The organic layer was acidified to pH 2 with 10% HCl. The organic layer was separated and aqueous layer washed with chloroform. This aqueous portion was basified with solid sodium bicarbonate to pH 8 and was extracted with chloroform. The chloroform layer was evaporated to yield an amorphous solid powder (7.14 g, 30% yield), purity 99.3.

EXAMPLE 4

Piperazine (12.4 g, 0.144 moles) and ethyl 2,3-dihydrobenzo[1,4]dioxin-2-carboxylate(20 g, 0.096 moles) were taken into a round bottom flask provided with a stirrer, thermowell and distillation setup. The reaction mixture was heated for 10 h to reach an internal temperature of about 75° C. while stirring. It was cooled to room temperature, dissolved in chloroform and washed with saturated sodium bicarbonate solution followed by water. The organic layer was acidified to pH 2 with 10% HCl. The organic layer was separated and aqueous layer washed with chloroform. This aqueous portion was basified with sodium bicarbonate to pH 8 and was extracted with chloroform. The chloroform layer was evaporated to yield an amorphous solid powder (10.7 g, 45% yield), purity 99.6%.

EXAMPLE 5

Into a round bottom flask provided with a stirrer, thermowell and distillation set up were taken piperazine (5.5 g, 0.064 moles) and ethyl 2,3-dihydrobenzo[1,4]dioxin-2-carboxylate (20 g, 0.096 moles). The reaction mixture is heated for 10 h to reach an internal temperature of about 75° C. while stirring. It was cooled to room temperature, dissolved in chloroform and washed with saturated sodium bicarbonate solution followed by water. The organic layer was acidified to pH 2 with 10% HCl. The organic layer was separated and aqueous layer washed with chloroform. This aqueous portion was basified with solid sodium bicarbonate to pH 8 and was extracted with chloroform. The chloroform layer was evaporated to yield an amorphous solid powder (7.5 g, 31.5% yield), purity 99.45%.

The advantages of the present invention are:
1. It is a very convenient process in which the bis-amide is easily separated by acid treatment of the reaction mixture of N-(2,3-Dihydrobenzo[1,4]dioxin-2-carbonyl) piperazine.
2. N-(2,3-Dihydrobenzo[1,4]dioxin-2-carbonyl)piperazine prepared by this method when coupled with 4-amino-2-chloro-6,7-dimethoxy quinazoline, gives the HCl salt which on basification affords 99.99% pure doxazocin base.
3. The doxazocin base thus obtained can be used without any further purification to get doxazocin mesylate with purity (99.99%) as required by the pharmaceutical industry.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and,scope of the invention as described in the following claims.

What is claimed is:

1. A process for the preparation of N-(2,3-Dihydrobenzo[1,4]dioxin-2-carbonyl)piperazine which comprises heating a reaction mixture ethyl of 2,3-dihydrobenzo[1,4]dioxin-2-carboxylate and piperazine with a molar ratio of carboxylate to piperazine in the range of 1:2 to 2:1, under nitrogen atmosphere, at a temperature in the range of 70–90° C. for a period of 3–15 hrs, cooling the above said reaction mixture to a temperature of 25–30° C. and dissolving it in chloroform followed by washing with saturated sodium bi-carbonate solution and water respectively, acidifying the organic layer by about 10% HCl to a pH ranging between 1 to 4, separating the organic layer and washing the aqueous layer with chloroform, basifying the aqueous layer with sodium bi-carbonate to a pH ranging between 7 to 9 followed by extracting with chloroform and evaporating the chloroform to obtain the final desired product in amorphous solid form.

2. A process as claimed in claim 1, wherein the reaction mixture is heated for a period of about 5 to about 12 hrs.

3. A process as claimed in claim 1, wherein the reaction temperature used is preferably in the range of 75–80° C.

4. A process as claimed in claim 1, wherein the purity of the compound N-(2,3-Dihydrobenzo[1,4]dioxin-2-carbonyl) piperazine obtained is in the range of 99.3–99.9%.

* * * * *